United States Patent
Shastri et al.

(10) Patent No.: US 6,582,717 B1
(45) Date of Patent: Jun. 24, 2003

(54) DRUG DELIVERY COMPOSITION AND DEVICE

(75) Inventors: Venkatram R. Shastri, Randolph, MA (US); Isaac Yue, Boston, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/543,964

(22) Filed: Apr. 7, 2000

(51) Int. Cl.⁷ ............................... A61F 2/00; A61K 9/14
(52) U.S. Cl. ........................ 424/426; 424/423; 424/486
(58) Field of Search .................................. 424/426, 423, 424/486, 49

(56) References Cited

U.S. PATENT DOCUMENTS 5,747,058 A  *  5/1998  Tipton et al. ................ 424/423
5,851,551 A  *  12/1998  Tseng et al. ................. 424/486
5,945,087 A  *  8/1999  Nelson et al. ................. 424/49

FOREIGN PATENT DOCUMENTS

WO        WO 97/41843      11/1997
WO        WO 99/61062      12/1999

OTHER PUBLICATIONS

Nagaraju, et al. "Biodegradable Dental Implants Containing Inclusion Complexes of Ciprofloxacin and Norfloxacin With β–Cyclodextrin" *Indian Drugs* 35(10):662–664, 1998.
Nagaraju, et al. "Biodegradable Dental Implants of Ciprofloxacin β–Cyclodextrin Inclusion Complex in the Treatment of Periodontitis" *Indian Journal of Experimental Biology* 37:305–307, 1999.

* cited by examiner

*Primary Examiner*—Thurman K. Page
*Assistant Examiner*—Blessing Fubara
(74) *Attorney, Agent, or Firm*—Choate, Hall & Stewart

(57) ABSTRACT

Drug delivery composition. The composition includes a polymeric material, a complexing agent, and a bioactive agent complexed with the complexing agent. The polymeric material, the complexing agent and the bioactive agent are formed into a delivery matrix. The delivery matrix is particularly adapted for placement below the gum line in a periodontal cavity.

18 Claims, 13 Drawing Sheets

R = H, Glycolide
R = CH$_3$, Lactide

FIG. 3
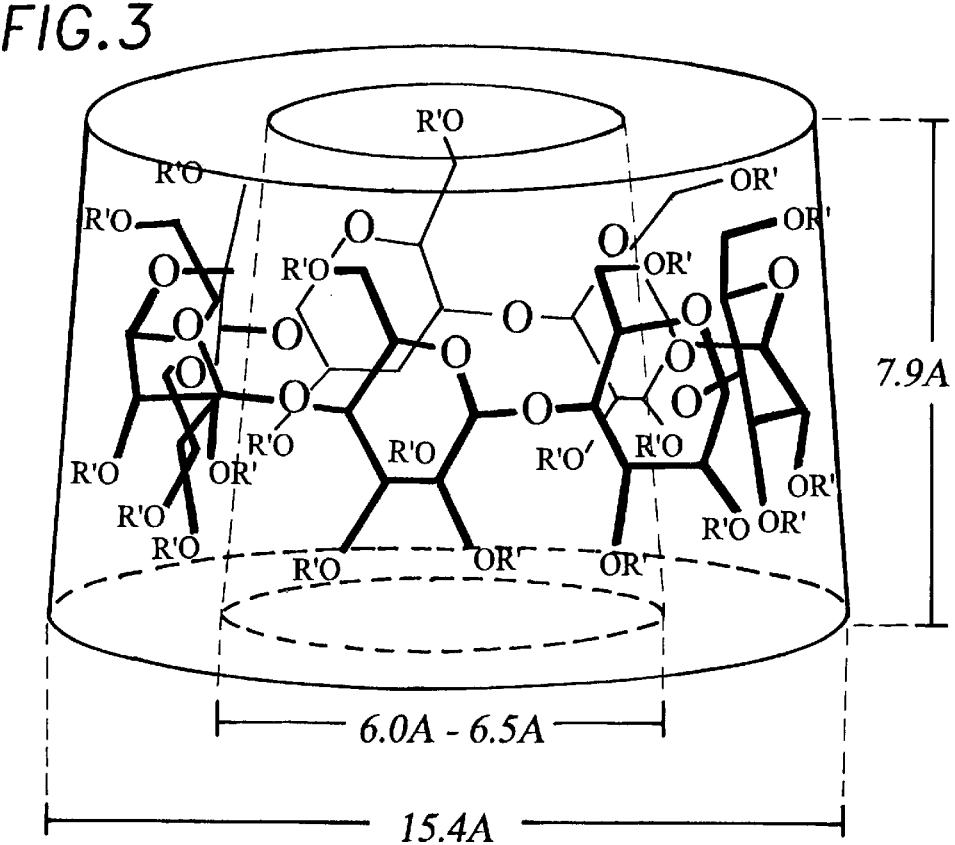
FIG. 4    Complexation and Release
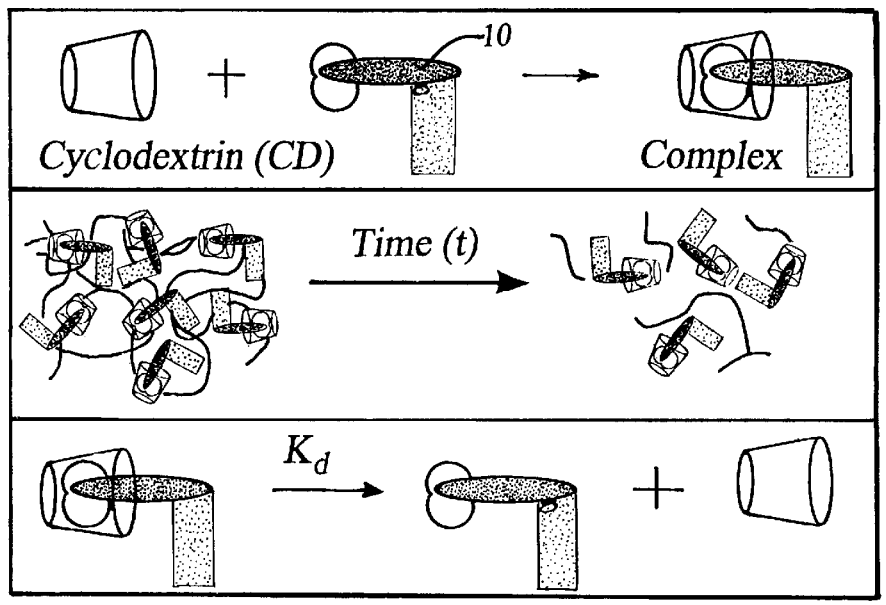

DRUG DELIVERY COMPOSITION AND DEVICE

The government has rights in this invention pursuant to NSF Grant No. 9525913.

BACKGROUND OF THE INVENTION

This invention relates to drug delivery compositions and devices and more particularly to polymeric compositions and devices for the delivery of bioactive agents to the periodontal pocket.

Periodontal disease often arises from the presence of pathogenic bacteria in the gingival pocket surrounding teeth. Disease arising from the pathogenic bacteria is treated with anti-microbial agents that are delivered in a variety of irrigation, systemic delivery and controlled delivery. Mouth rinses are relatively poor at reaching the site of the disease activity but good in providing adequate drug concentration. The duration of therapy is poor while patient compliance is fair. Subgingival irrigation is good in reaching the site of disease activity and providing adequate drug concentration but provides poor duration of therapy and only fair patient compliance. Systemic delivery is good at reaching the site of the disease activity but provides only fair drug concentration, duration of therapy and patient compliance. In contrast, controlled drug delivery would be characterized as good in each of the categories.

Current delivery systems include a collagen-based Periochip™ which is easy to insert into the gingival pocket but provides a sub-optimal release profile, is difficult to place when wet and has limited efficacy. Atridox™ injectable polymer is easily placed but has limited efficacy, is difficult to retrieve and generates systemic effects. Actisite™ EVAC (LVAX) fiber is efficacious but is difficult to place.

It is therefore an object of the present invention to develop a drug delivery system that will provide improved encapsulation efficiency and release characteristics of anti-microbials in a polymeric delivery system. The system will allow for easy manipulation of drug lipophilicity, protect the drug from premature degradation and be easily adapted to various delivery device configurations.

SUMMARY OF THE INVENTION

The drug delivery composition of the invention includes a polymeric material, a complexing agent, and a bioactive agent complexed with the complexing agent. The polymeric material, the complexing agent, and the bioactive agent are formed into a delivery matrix or chip.

In a preferred embodiment, the complexing agent has a hydrophobic core and a hydrophilic exterior. A suitable complexing agent is β-cyclodextrin which may be methyl-β-cyclodextrin or hydroxy-propyl β-cyclodextrin or any derivatives thereof. The bioactive agent may be a hydrophobic anti-microbial such as chlorhexidine or chlorhexidine digluconate. Other suitable anti-microbials include tetracycline, tobramycin and gentamicin. A suitable polymeric material PLGA co-polymer. Other polymers ate suitable such as photoreactive polymers. The drug delivery composition may also include water-soluble additives such as sugars, salts or poly (ethylene oxide) and derivatives and co-polymers thereof. Poly (ethylene glycol) is also suitable.

A preferred embodiment of the drug delivery composition of the invention includes PLGA co-polymer, cyclodextrin, and chlorhexidine or chlorhexidine digluconate complexed. with the cyclodextrin. The composition is compressed to form a delivery matrix such as a chip.

The drug delivery composition of the invention allows for the delivery of hydrophobic drugs, controls burst effect and increases encapsulation efficiency. The complexing agent protects the drug and alters solubility and lipophilicity of the drug. The use of PLGA allows a steady state release profile.

BRIEF DESCRIPTION OF THE DRAWINGS

FIG. 3 is a structural diagram of β-cyclodextrin.

FIG. 4 is a schematic diagram illustrating complexation and release.

DESCRIPTION OF THE PREFERRED EMBODIMENT

Figure 1:
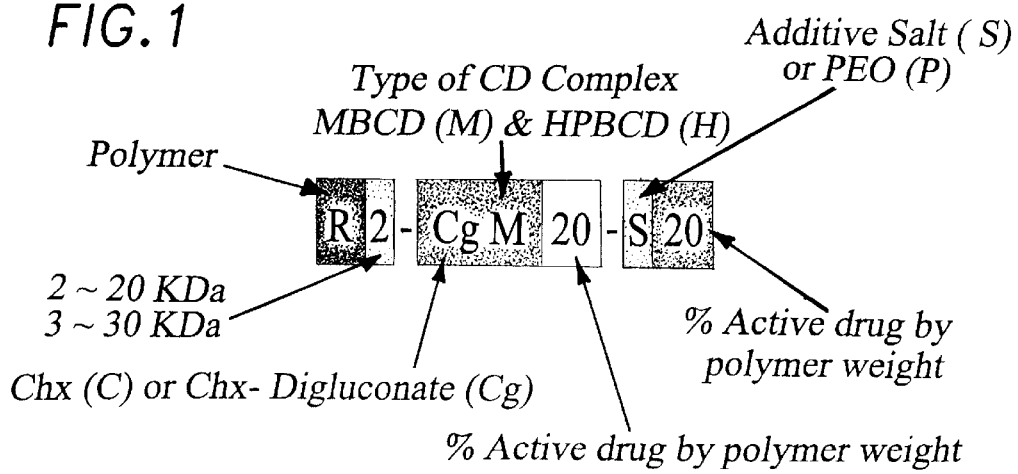
FIG. 1 is a schematic illustration of the composition of the invention.

FIG. 1 illustrates a preferred embodiment of the present invention. In FIG. 1, R refers to a polymer such as PLGA co-polymer. As shown, the polymer may have a weight of approximately 20 KDa or 30 KDa. A drug to be delivered is represented by $C_g$ and may be chlorhexidine (Chx) or chlorhexidine digluconate (Chx-Dg). Cyclodextrin is represented by M or H for methylated β-cyclodextrin or hydroxy-propyl β-cyclodextrin, respectively. The active drug percentage by polymer weight is illustrated by the numeral such as 20. Additive water soluble sugars, salts or poly (ethylene oxide) are shown in the figure by S and the numeral 20 adjacent to S (or P) represents the percentage additive by polymer weight.

Figure 2:
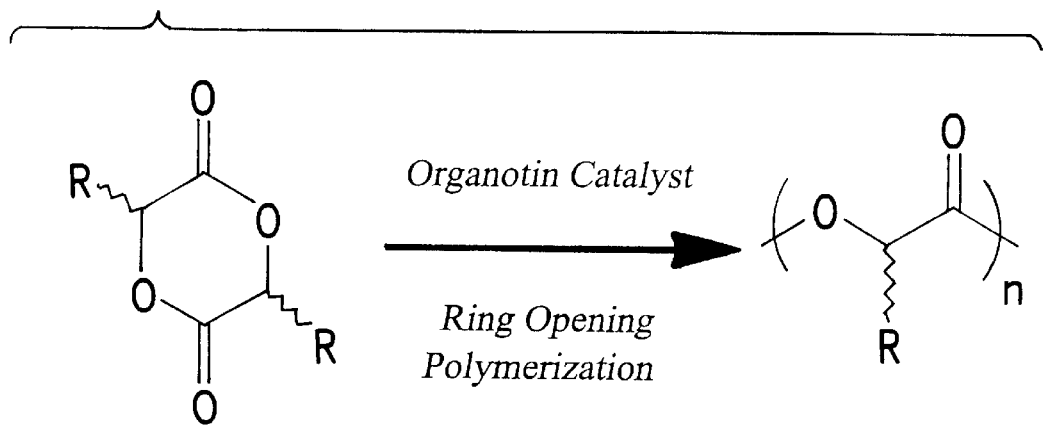
FIG. 2 is a diagram illustrating synthesis and structure of poly (alpha-hydroxy) acids (PLGA).

FIG. 2 illustrates the synthesis and structure of poly (alpha-hydroxy) acids known as PLGA. As shown, a catalyst opens the ring to allow polymerization. FIG. 3 shows the structure of β-cyclodextrin which those skilled in the art will appreciate has a hydrophobic core and a hydrophilic exterior. This structure can form supramolecular host-guest inclusion complexes.

As shown in FIG. 4, cyclodextrin will complex with a drug 10. When the complexed material is in, for example, a gingival pocket at physiological pH the drug will be released from the cyclodextrin as illustrated.

Figure 5:
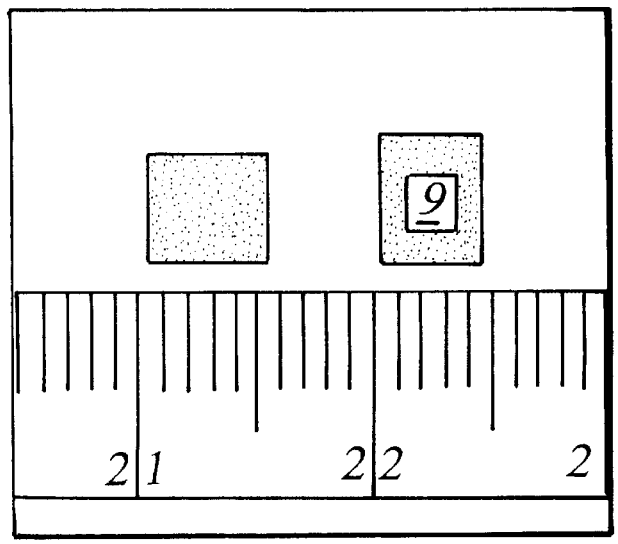
FIG. 5 is a plan view of the drug delivery chips of the invention.
Figure 6:
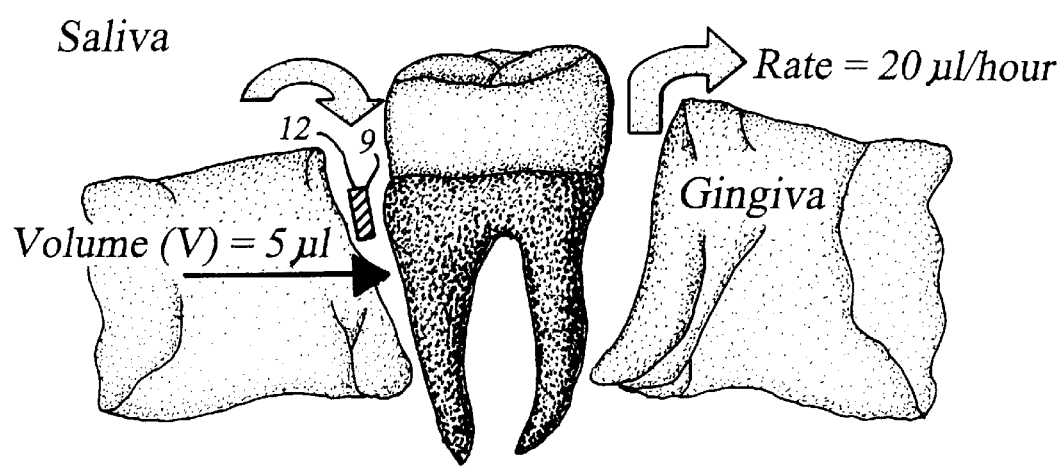
FIG. 6 is a schematic illustration of a tooth and gingival pocket.

The delivery device of the invention was prepared by compression (20,000 pounds per square centimeter for five minutes) of microspheres or a physical mixture of the desired components such as those illustrated in FIG. 1. The resulting device is in the form of a chip 9 as shown in FIG. 5 adjacent to a scale for size comparison. The chips are approximately 5 mm×4 mm and approximately 0.5 mm thick. A chip 9 from FIG. 5 would be placed into a gingival pocket or cavity 12 below the gum line as shown in FIG. 6 to treat a microbial infection.

The drug delivery matrix of the invention has been tested by placing a 10 mg chip in a 1 mL phosphate buffer saline (PBS) solution having a pH of 7.4. The PBS solution is analyzed and replaced everyday. The released chlorhexidine (or derivative) was then analyzed by reverse phase HPLC.

The drug delivery compositions of the invention may be made by several techniques. In one technique, the constituent materials are simply mixed together and compressed to form the delivery matrix or chip as discussed above. In another technique, one can first form the chlorhexidine/cyclodextrin complex and then add the complex to a polymer dissolved in a solvent. Those skilled in the art will appreciate that the resulting emulsion can be processed to provide microspheres. A single or double emulsion process may be used. The delivery matrix may be made by any suitable free form fabrication technique such as powder sintering and three-dimensional printing.

Figure 7A:
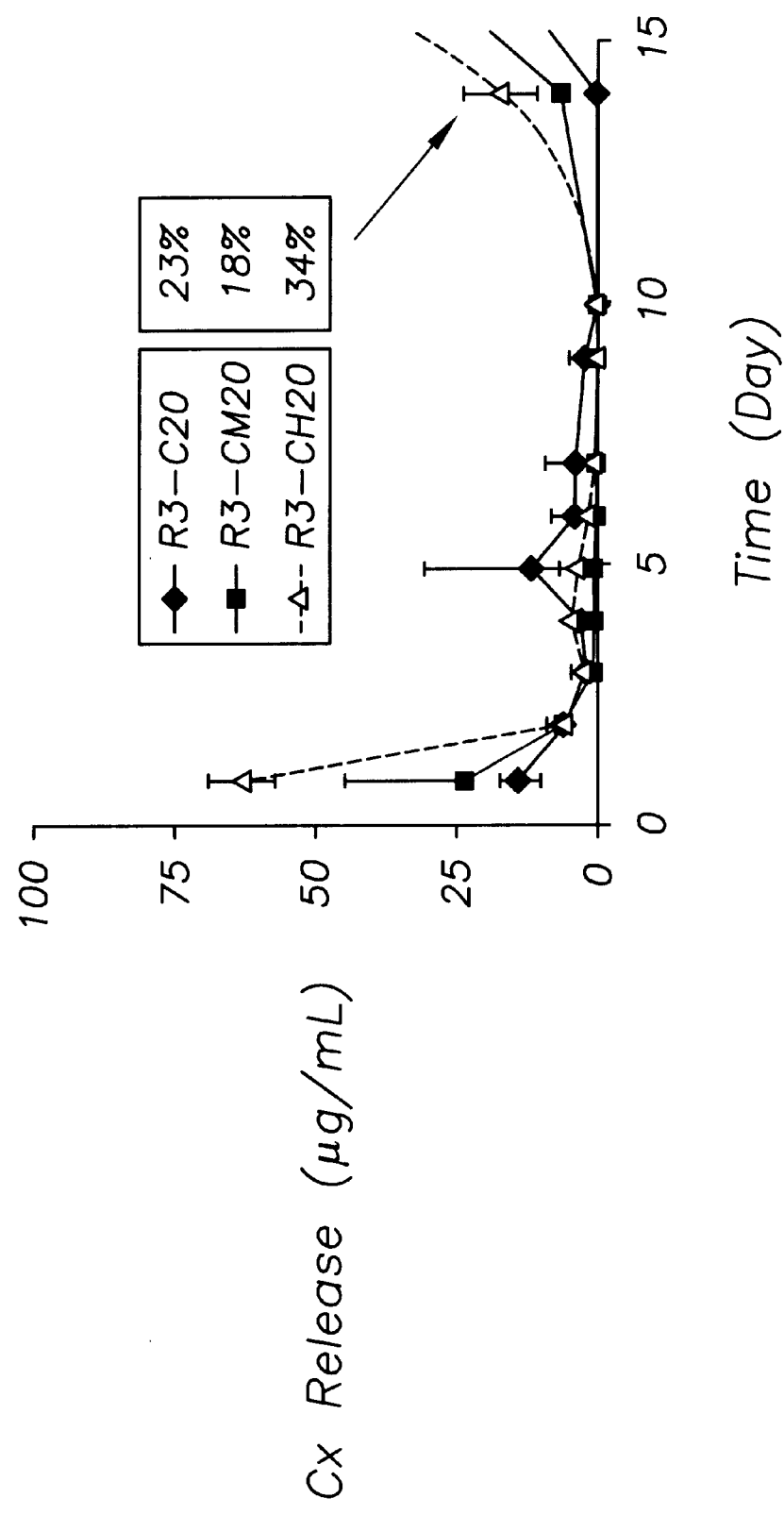
FIG. 7 is a graph of drug release as a function of time.
Figure 7B:
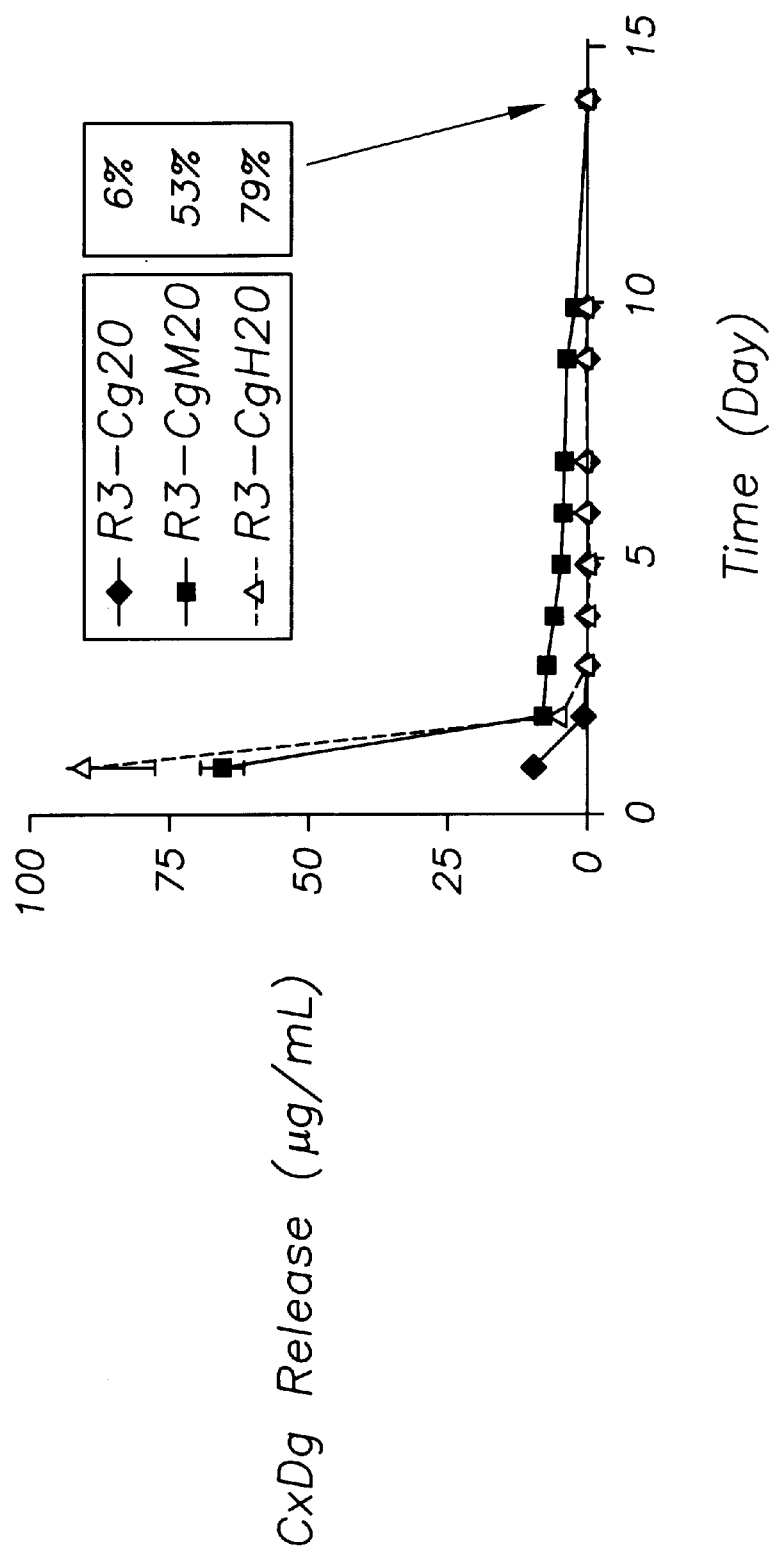

FIG. 7 shows the effect of cyclodextrin on drug release as a function of time. The Table below shows the encapsulation efficiency for the material illustrated in FIG. 7.

|  | Encapsulation Efficiency (%) | | |
| --- | --- | --- | --- |
|  | PGLA | PLGA and Methylated β-Cyclodextrin | PLGA and Hydroxy-propyl β-Cyclodextrin |
| Chx | 185.7 μg (9.28%) | 180.5 μg (9.02%) | 302.8 μg (15.1%) |
| ChxDg | 204.7 μg (10.2%) | 230.3 μg (11.5%) | 121.2 μg (6.1%) |

Figure 8:
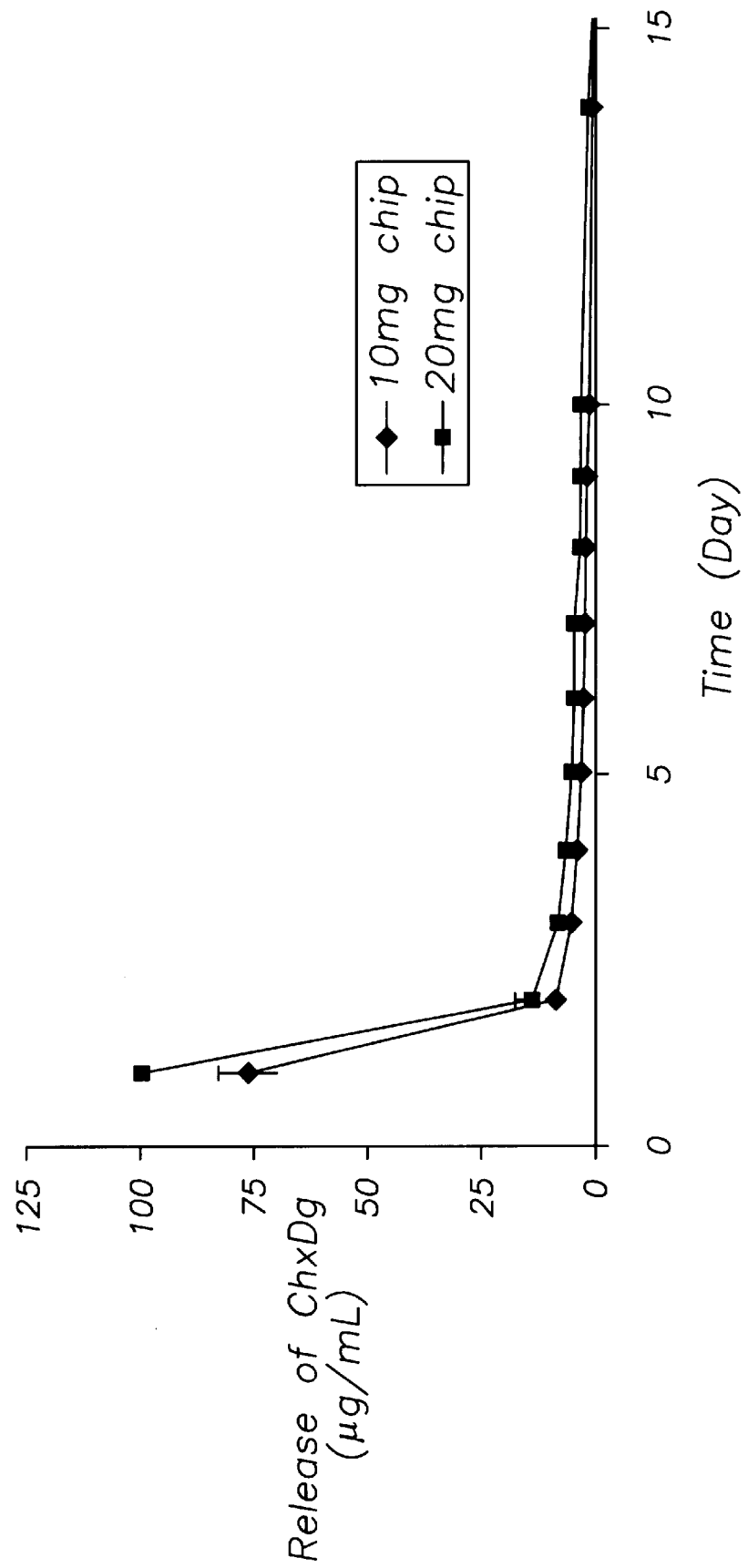
FIG. 8 is a graph of drug release versus time as a finction of cyclodextrin mass.
Figure 9A:
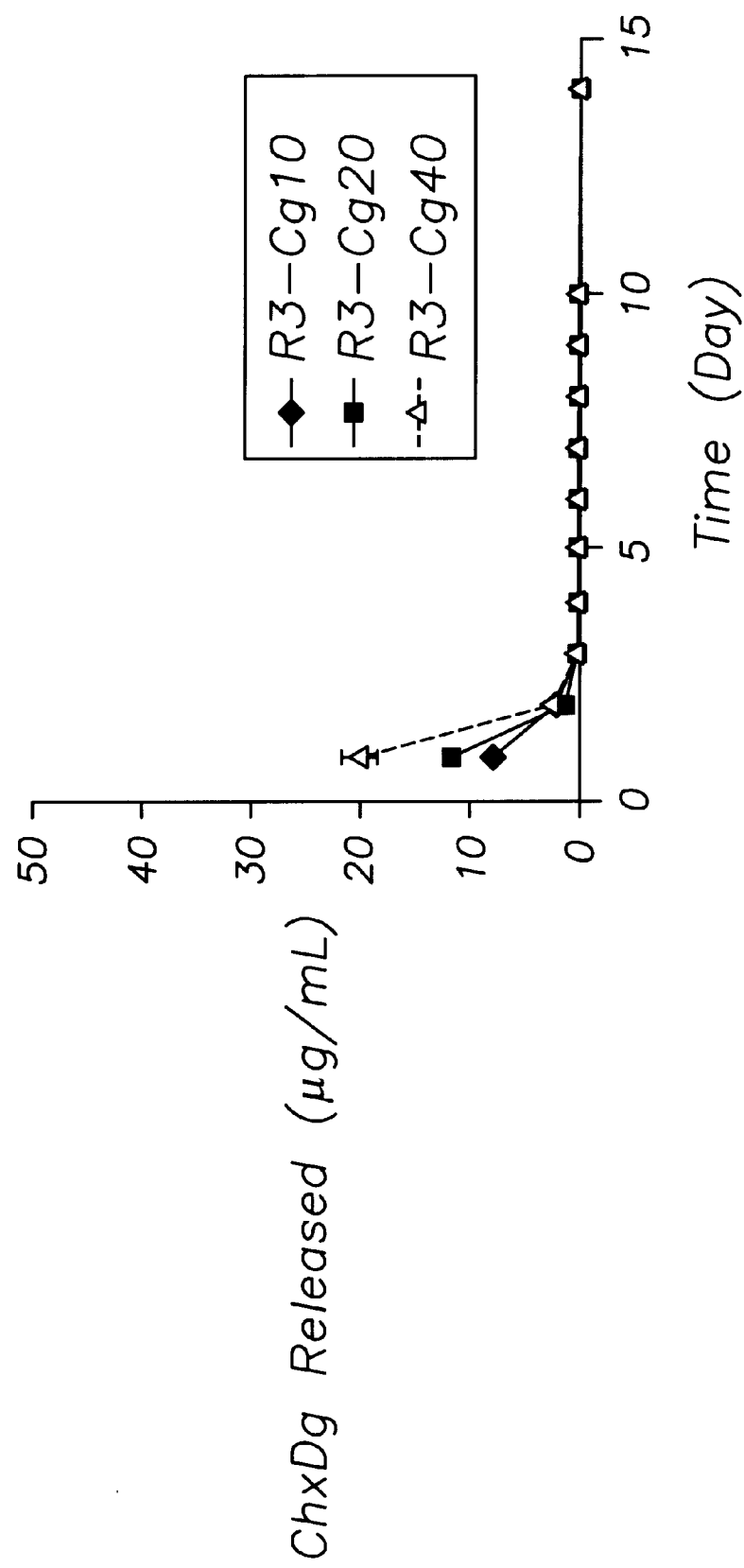
FIG. 9 is graph illustrating the effect of varying chlorhexidine digluconate and chlorhexidine digluconate methyl-β-cyclodextrin loading on burst.
Figure 9B:
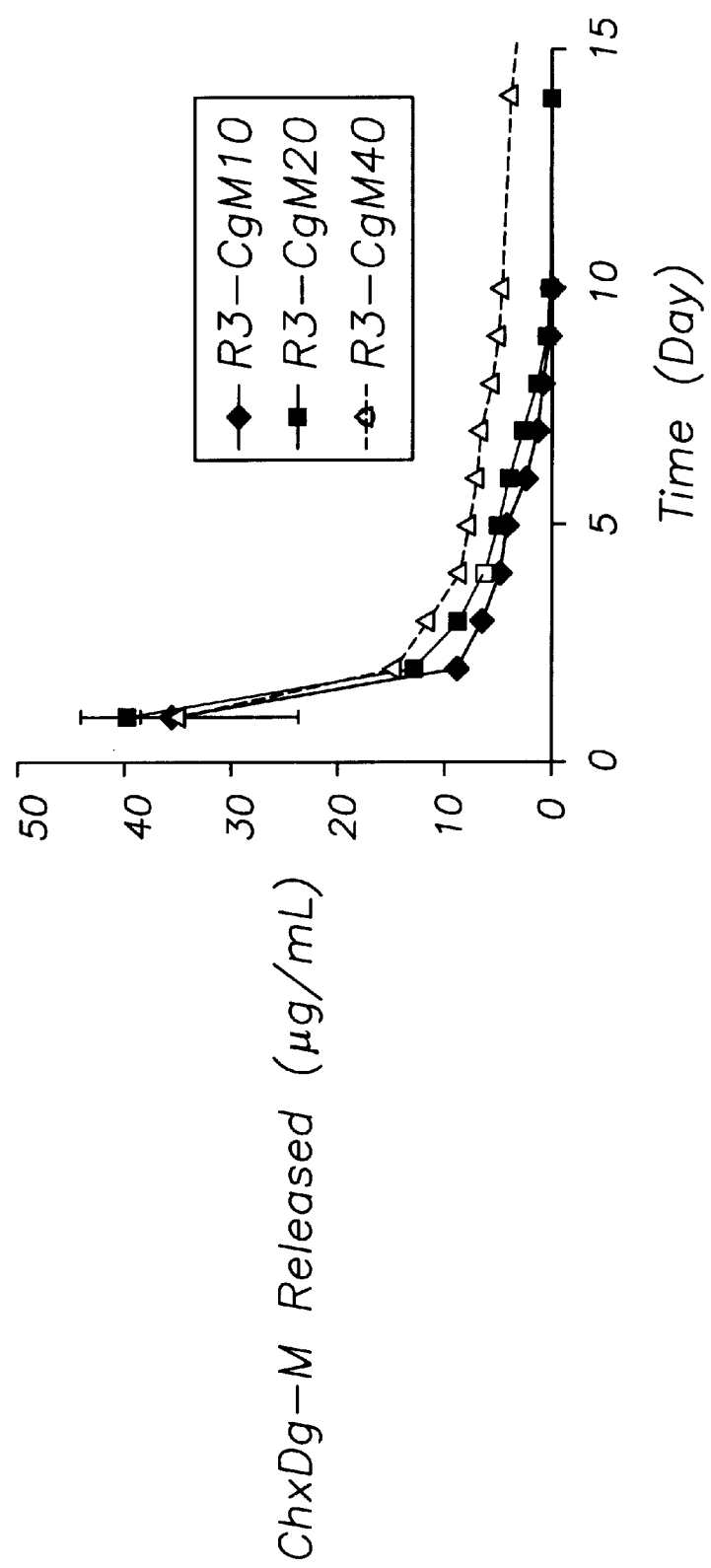
Figure 10:
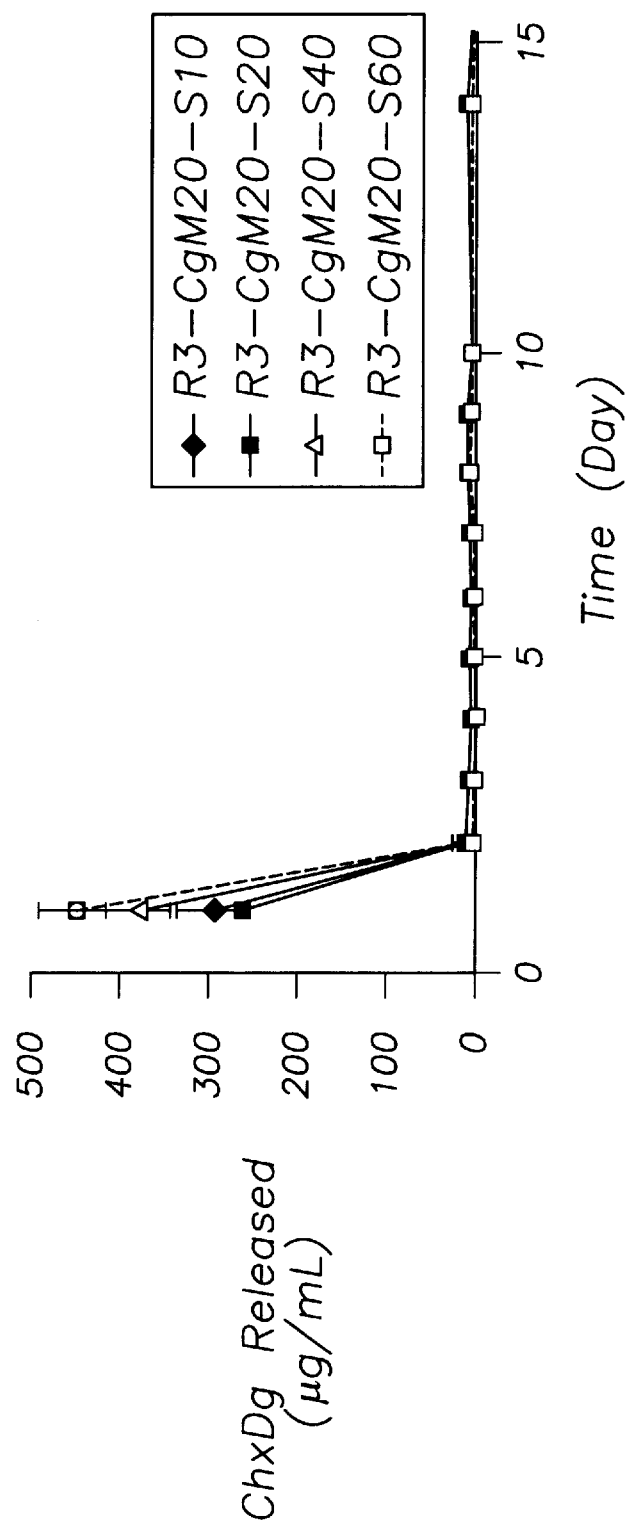
FIG. 10 is a graph illustrating chlorhexidine digluconate release from PLGA/cyclodextrin chips with varying salt concentrations.
Figure 11:
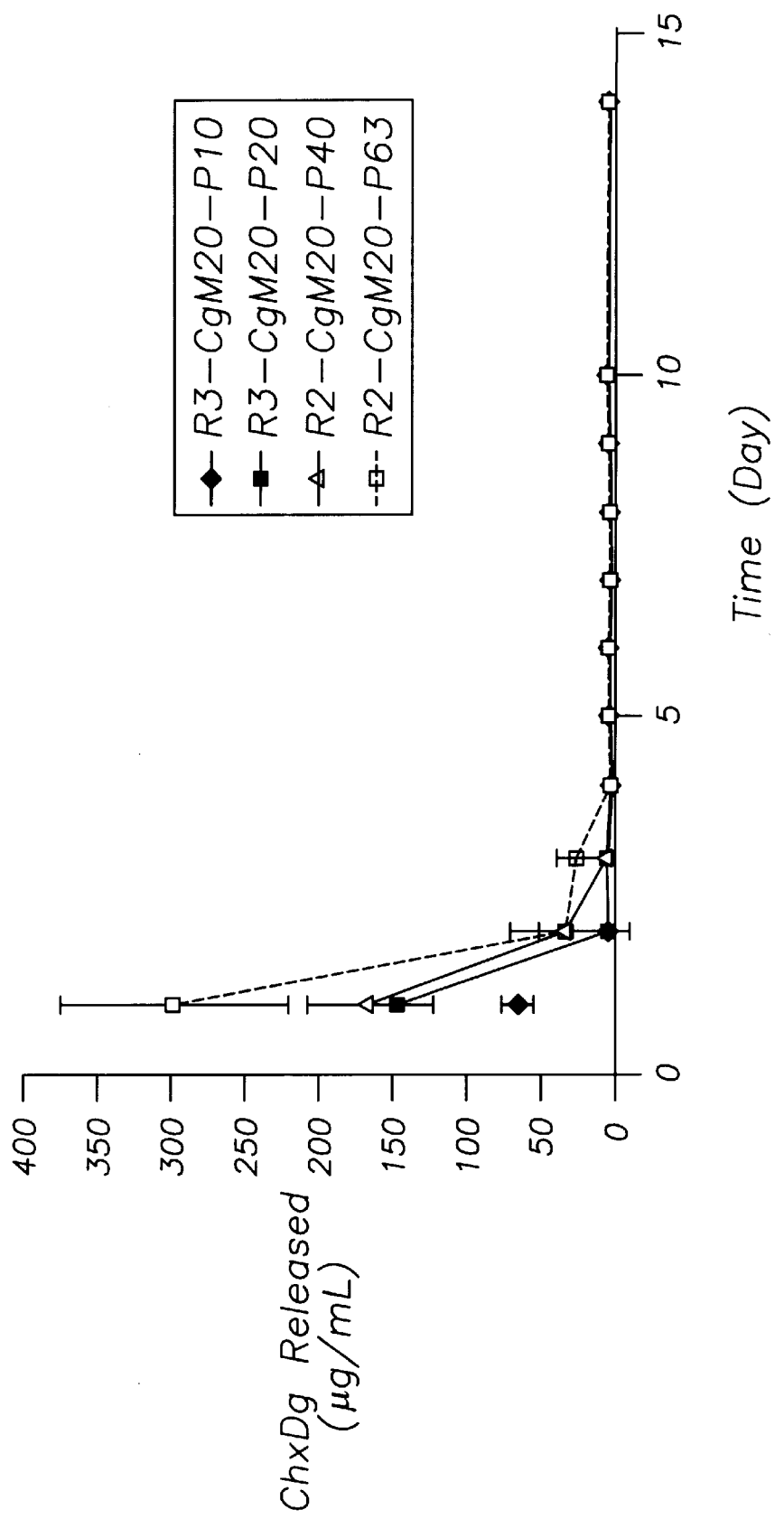
FIG. 11 is a graph illustrating release of chlorhexidine digluconate with varying concentration of poly (ethylene oxide).
Figure 12:
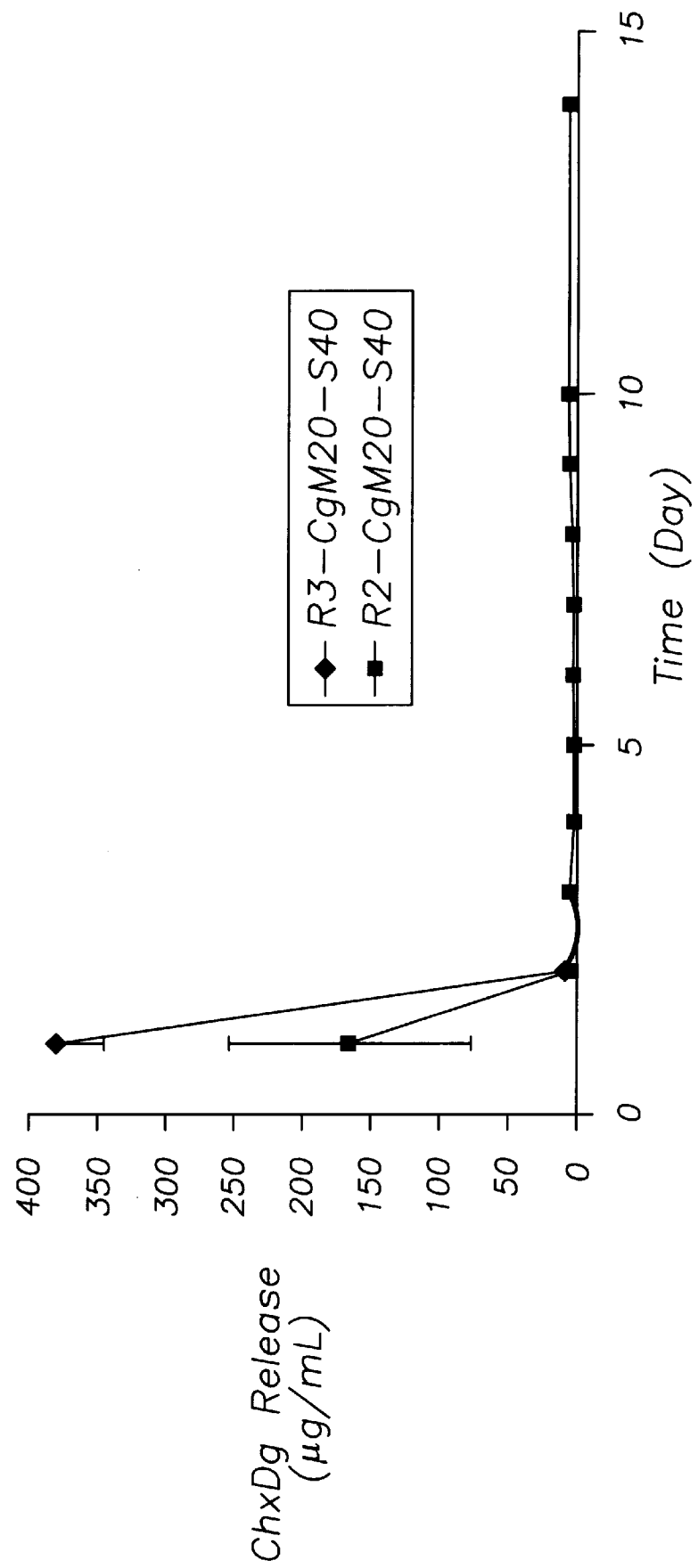
FIG. 12 is a graph illustrating the effect of PLGA on chlorhexidine digluconate release.

FIG. 8 illustrates the effect of the chlorhexidine digluconate-cyclodextrin complex mass on release. Similarly, FIG. 9 shows the effect of varying chlorhexidine digluconate and chlorhexidine digluconate-cyclodextrin loading on burst, that is, the initial amount of drug that is released. FIGS. 10 and 11 illustrate release characteristics with varying salt and PEO concentration. FIG. 12 illustrates the effect of PLGA on chlorhexidine digluconate release.

Figure 13:
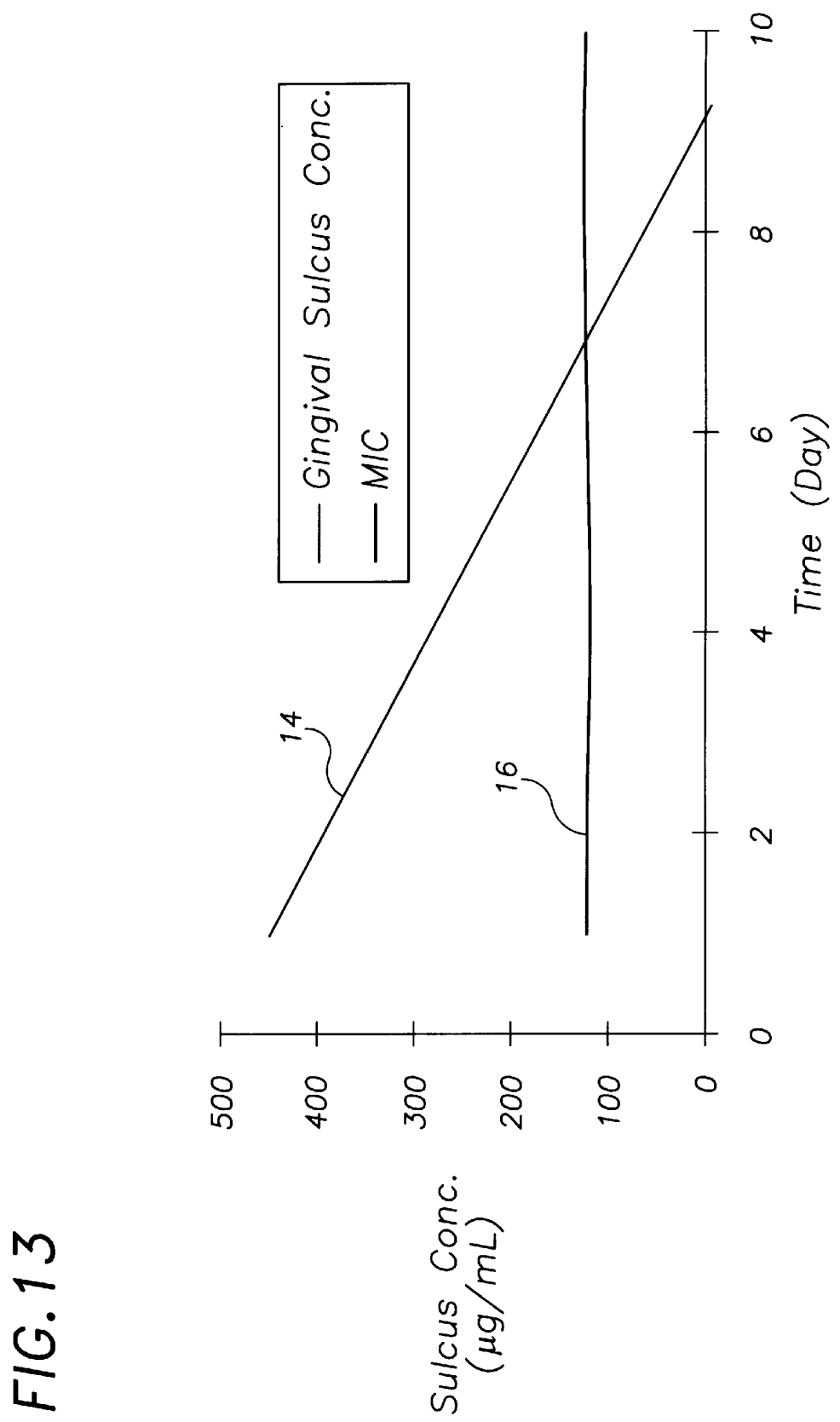
FIG. 13 is a graph of sulcus concentration as a function of time.

FIG. 13 is a theoretical model of the system of the invention which shows gingival sulcus concentration 14 as a finction of time. Also included is the minimum inhibitory concentration 16. This chart shows that the present invention is effective for at least approximately one week.

Figure 14:
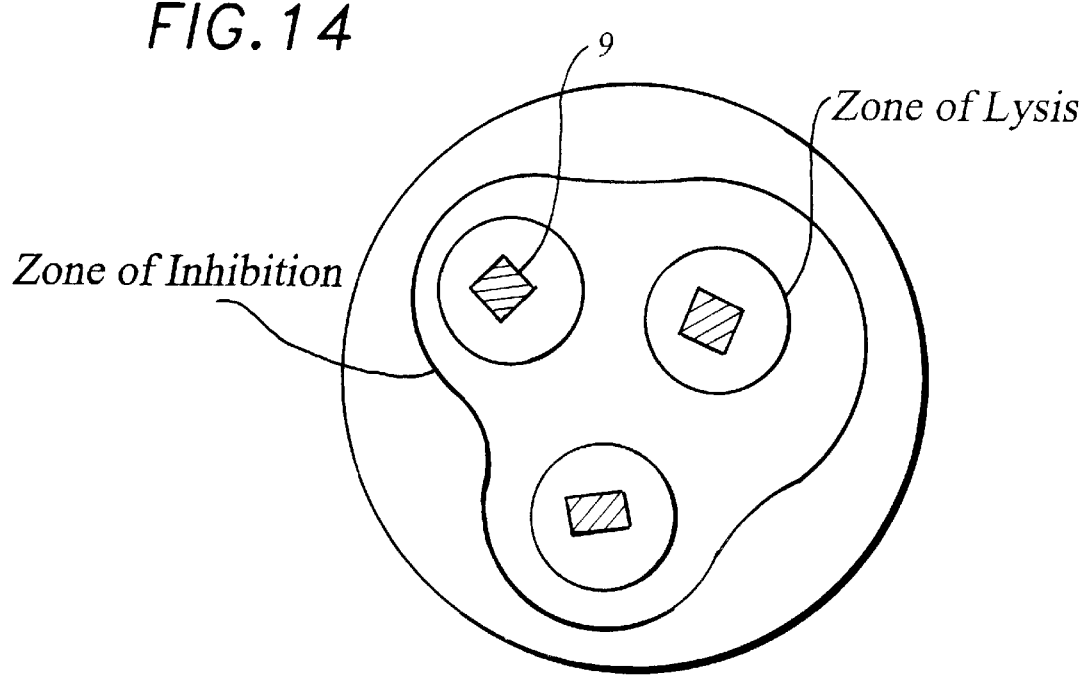
FIG. 14 is an illustration of the anti-microbial effects of the invention.

FIG. 14 illustrates the zone of lysis and the zone of inhibition provided by chips of the invention on an agar plate.

It is thus seen that the delivery matrix of the invention allows for the delivery of hydrophobic drugs with good control over the burst effect and with increased encapsulation efficiency. The use of a polymer such as PLGA allows a steady state release profile.

It is recognized that modifications and variations of the invention disclosed herein will become apparent to those skilled in the art and it is intended that all such modifications and variations be included within the scope of the appended claims:

What is claimed is:

1. Drug delivery composition comprising:

a polymeric material;

a complexing agent; and a bioactive agent complexed with the complexing agent, the polymeric material, complexing agent and bioactive agent formed into a chip.

2. The drug delivery composition of claim 1 wherein the complexing agent has a hydrophobic core and hydrophilic exterior.

3. The drug delivery composition of claim 2 wherein the complexing agent is β-cyclodextrin.

4. The drug delivery composition of claim 2 wherein the complexing agent is methylated β-cyclodextrin.

5. The drug delivery composition of claim 2 wherein the complexing agent is hydroxy-propyl β-cyclodextrin.

6. The drug delivery composition of claim 2 wherein the bioactive agent is hydrophobic.

7. The drug delivery composition of claim 1 wherein the polymeric material is polyglycolic-co-lactic acid (PLGA) co-polymer.

8. The drug delivery composition of claim 1 wherein the bioactive agent is an anti-microbial.

9. The drug delivery composition of claim 8 wherein the anti-microbial is chlorhexidine.

10. The drug delivery composition of claim 8 wherein the anti-microbial is chlorhexidine digluconate.

11. The drug delivery composition of claim 1 further including a water-soluble additive.

12. The drug delivery composition of claim 11 wherein the additive is a salt.

13. The drug delivery composition of claim 11 wherein the additive is poly (ethylene oxide).

14. The drug delivery composition of claim 1 wherein the bioactive agent is approximately 20% by weight of the polymer weight.

15. The drug delivery composition of claim 1 wherein the polymer weight is approximately 20 KDa.

16. The drug delivery composition of claim 1, wherein the polymer weight is approximately 30 KDa.

17. The drug delivery composition of claim 11 wherein the additive is in the range of 10–60% by weight of the polymer weight.

18. The drug delivery composition of claim 1 adapted for insertion into a periodontal cavity.

* * * * *